United States Patent [19] [11] 4,343,308
Gross [45] Aug. 10, 1982

[54] SURGICAL GROUND DETECTOR

[76] Inventor: Robert D. Gross, 5427 6th St., Lubbock, Tex. 79416

[21] Appl. No.: 157,403

[22] Filed: Jun. 9, 1980

[51] Int. Cl.³ .............................................. A61B 17/39
[52] U.S. Cl. ............................................. 128/303.13
[58] Field of Search ...................... 128/303.13, 303.14, 128/303.17, 303.18, 736, 783, 798, 802, 803

[56] References Cited

U.S. PATENT DOCUMENTS 3,601,126  8/1971  Estes ............................... 128/303.14
3,634,652  1/1972  Shimizu et al. ............ 128/303.18 X
3,683,923  8/1972  Anderson ....................... 128/303.14
3,848,600  11/1974  Patrick, Jr. et al. ........... 128/303.13

FOREIGN PATENT DOCUMENTS 855459  11/1960  United Kingdom ........... 128/303.17

Primary Examiner—Lee S. Cohen
Attorney, Agent, or Firm—Wendell Coffee

[57] ABSTRACT

An electrosurgical grounding pad has a temperature sensor to prevent skin burns. A paraffin insulated conductor is embedded in a conducting gel medium so that before a burn-producing temperature exists, the insulation melts and connects the conductor to ground. An alarm detects the presence of the ground and alerts operating room personnel of the burn condition.

9 Claims, 4 Drawing Figures

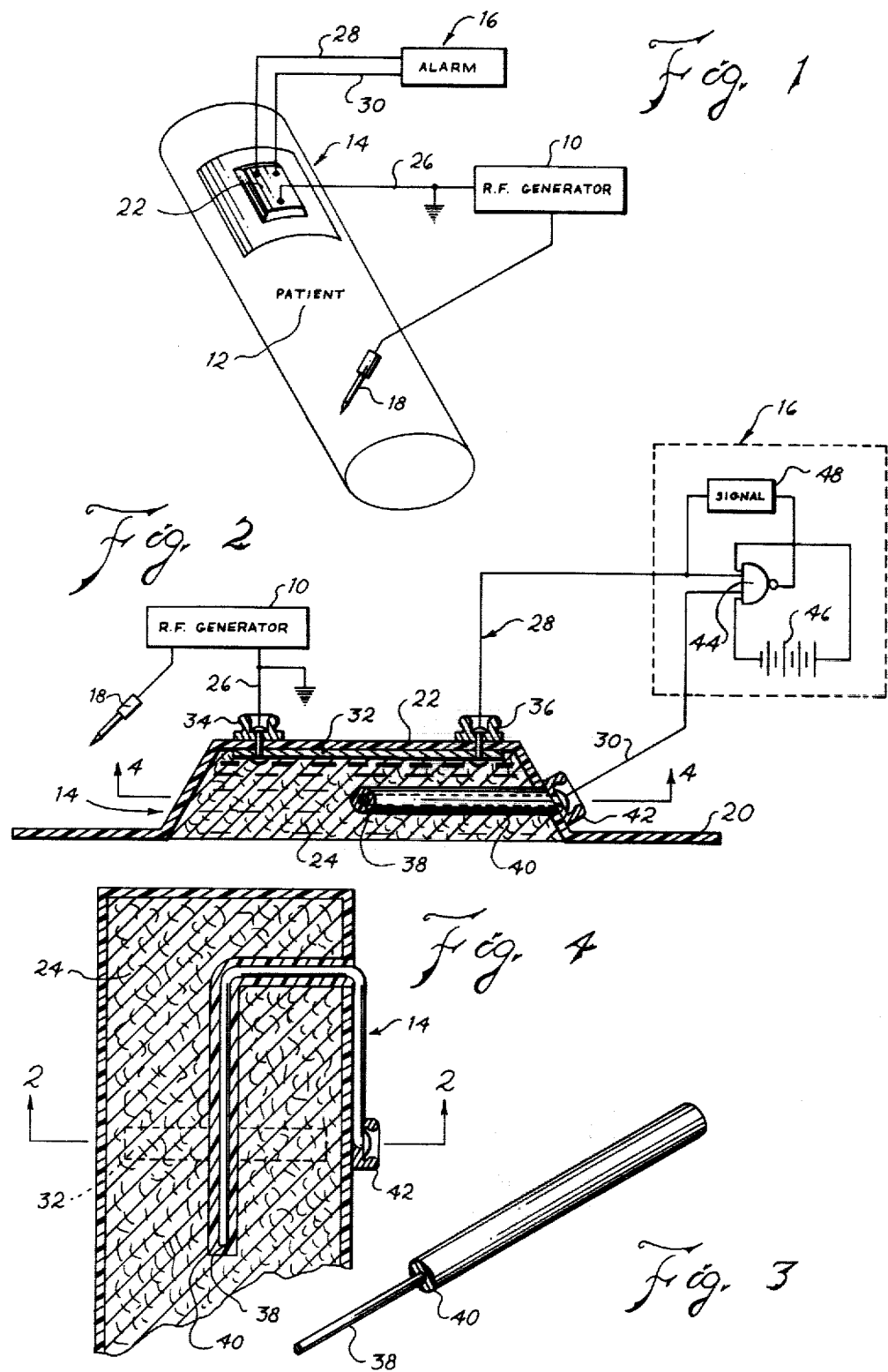

SURGICAL GROUND DETECTOR

BACKGROUND OF THE INVENTION (1) Field of the Invention

This invention relates to electrosurgery and more particularly preventing grounding pad burns on a patient.

(2) Description of the Prior Art

Those skilled in the art of electrosurgery are familiar with the problem of severe burns to the patient at the location of attached grounding pads. A radio frequency (RF) source utilizes a high density current for localized coagulating or cutting. Grounding pads are connected to the patient who must be at a zero or ground potential electrically.

Several devices have previously attempted to solve the problem associated with an inactive electrode ground plate. All of these devices utilize the common design of measuring a change in current resulting from the loss of a solid ground connection to the patient.

Before this application was filed, applicant caused a search to be made in the U.S. Patent and Trademark Office at which time all of the following patents were found:

HOOD, U.S. Pat. No. 2,660,717
CROWLEY, U.S. Pat. No. 3,628,093
ANDERSON, U.S. Pat. No. 3,683,923
NEWTON, U.S. Pat. No. 4,094,320
GONSER, U.S. Pat. No. 4,121,590
BLACKETT, U.S. Pat. No. 4,122,854

The NEWTON patent, which was assigned to Valleylab, Inc., utilizes a complex electronic circuit to monitor currents associated with a ground plate. The BLACKETT patent, which was assigned to Matburn (Holdings) Limited, uses a voltage sensitive circuit while the patient is grounded by a ground plate. Similarly, ANDERSON, which was assigned to Valleylab, Inc., utilizes a current sensing circuit for use with a grounding plate. CROWLEY discloses a temperature responsive protection system for electric appliances (blanket) and is not related to the medical profession. GONSER, which was assigned to Dentaply Research and Development Corporation, utilizes a voltage and current limiting circuit where a ground plate is used. HOOD does not appear to be pertinent to applicant.

The prior art has consistently tried to solve the problem by measuring currents and voltages when a faulty patient ground existed.

SUMMARY OF THE INVENTION (1) New and Different Function

I have invented an electrosurgical ground detector which monitors a burn-producing temperature at the groundskin interface. The temperature sensor is connected to an alarm. Before a burn occurs on a patient who is grounded by a grounding pad, the skin and grounding pad temperature will greatly rise. The patient's skin heat is transferred through a grounding pad to melt a layer of paraffin insulation and connect two conductors. Thickness and composition of the insulation and wire determine the time required for the alarm to indicate a dangerous temperature on the skin surface.

Thus it may be seen that the total function of my invention far exceeds the sum of the functions of the individual wires, contacts, generator, wax, etc.

(2) Objects of this Invention

An object of this invention is to prevent an electrosurgical burn.

Further objects are to achieve the above with a device that is sturdy, compact, durable, lightweight, simple, safe, efficient, versatile, ecologically compatible, energy conserving, and reliable, yet inexpensive and easy to manufacture, install, operate and maintain.

Other objects are to achieve the above with a method that is versatile, ecologically compatible, energy conserving, rapid, efficient, and inexpensive, and does not require skilled people to install, operate, and maintain.

The specific nature of the invention, as well as other objects, uses, and advantages thereof, will clearly appear from the following description and from the accompanying drawing, the different views of which are not scale drawings.

BRIEF DESCRIPTION OF THE DRAWING

FIG. 1 is a perspective representation, schematic in character, showing my invention in use.

FIG. 2 is a cross sectional view of the grounding pad thereof with a schematic of the electrical apparatus.

FIG. 3 is a perspective view of an insulated wire thereof with the insulation broken away.

FIG. 4 is a sectional view of the grounding pad taken substantially on line 4—4 of FIG. 2.

DESCRIPTION OF THE PREFERRED EMBODIMENT

Referring to the drawings, there may be seen in FIG. 1 the coupling of an RF generator 10, a patient 12, a grounding pad 14 and an alarm circuit 16. An active electrode probe 18 connected to the generator is the tool used by the surgeon to cut or to coagulate during the surgery. Since the patient 12 is typically under anesthesia and unconscious during surgery, he is unable to warn operating room personnel that said grounding pad surface is hot or burning him. Outer band or perimeter 20 of grounding pad 14 is an adhesive surface which adheres to said patient's skin. Container 22 of grounding pad 14 is a conductive gel 24 which also adheres to the patient's skin.

Ground wire 26 connects the RF generator 10 to container 22. The ground wire 26 is a common ground of the hospital's electrical system. Referring to FIG. 2, ground wire 26 connects to RF ground contact 34 on pad 14 and to the gel 24 by metal strip 32. Alarm ground 28 links to ground wire 26 by metal strip 32 embedded in grounding pad 14. Alarm ground 28 connects to alarm ground contact 36 on pad 14. Since wires 26 and 28 are connected to system ground, contacts 34 and 36 are both male plugs. As a practical matter, it makes no difference whether RF generator 10 and alarm 16 connect male contacts 34 and 36 or vice versa. This eliminates confusion to operating room support personnel in connecting the apparatus.

Container 22 holds conductive gel 24 while also contains fabric support material. Before a burn can occur to the patient 12, sufficient heat must be present on the patient's skin. This heat originates or is transferred from the skin through the grounding pad 14. The presence of the heat may be detected by inserting a wire 38 into gel 24 with a coat of insulating wax 40 totally surrounding the wire 38 as seen in FIG. 4.

In FIG. 3 there may be seen a layer of wax 40 which is less than 0.5 mm in thickness around wire 38. The wax 40 insulates the wire 38 from conducting gel 24, ground wire 26, alarm ground 28 and strip 32. Wire 38 attaches to alarm wire 30 by alarm contact 42 which is a female contact on the pad 14. A measureable amount of resistance exists between alarm ground 28 and alarm wire 30. The alarm ground 28 and alarm wire 30 connect alarm 16 which is capable of being activated by a change in resistance. When the temperature rises sufficiently, the wax 40 melts and exposes wire 38 to the conducting gel 24 and ground wire 26. The resistance between the alarm ground 28 and alarm wire 30 becomes negligible since the alarm wire 30 is now connected to the system ground. This change causes the alarm 16 to activate.

The thickness of the wax coating 40 and wire 38 determines the amount of skin heat needed to melt the wax 40. The wax 40 is selected from a paraffin of the methane series. The melting point of these waxes varies a considerable amount. The melting point may be preset by choosing a methane compound with a varying number of carbon atoms. The following table lists varying compounds from Heneicosane, which has 21 carbon atoms and a melting point of 40° C., through Triacontane which has 30 carbon atoms and a melting point of 66.1° C. A methane compound with less than 23 carbon atoms is not recommended due to the low melting points. Methane compounds with 24 to 30 carbon atoms provide sufficient melting before a serious skin burn occurs.

| | | |
|---|---|---|
| $C_{21}H_{44}$ | Heneicosane | M.P. = 40° C. |
| $C_{22}H_{46}$ | Docosane | M.P. = 44.4° C. |
| $C_{23}H_{48}$ | Tricosane | M.P. = 47.7° C. |
| $C_{24}H_{50}$ | Tetracosane | M.P. = 51.1° C. |
| $C_{26}H_{54}$ | Isohexacosane | M.P. = 61° C. |
| $C_{27}H_{56}$ | Heptacosane | M.P. = 59.5° C. |
| $C_{30}H_{62}$ | Triacontane | M.P. = 66.1° C. |

Alarm ground 28 and alarm wire 30 attach to Nand gate 44. Signal 48, which may be a buzzer, light emitting diode, etc., connects the alarm ground 28 and the output of Nand gate 44. The output of Nand gate 44 remains at ground potential before the wax 40 melts. Once the wax 40 melts and the alarm wire 30 is at system ground potential, an output voltage is produced at the signal 48 by the Nand gate 44. The alarm 16 is actually detecting when a ground exists and activating a signal 48 in response. A battery 46 is needed to power the Nand gate 44 and signal 48. The alarm 16 is a self-contained device which can be placed to the side of the patient. As stated, the thickness and composition of the insulation and wire determine the time required for the alarm to indicate a dangerous temperature on the skin surface; therefore, the time the temperature exceeds the temperature limit before activating the alarm may be preset by choice of the composition and thickness of the insulation and wire.

An example of other alarms which would work just as well are those disclosed in U.S. Pat. Nos. 3,277,465 and 3,331,970.

The embodiment shown and described above is only exemplary. I do not claim to have invented all the parts, elements or steps described. Various modifications can be made in the construction, material, arrangement, and operation, and still be within the scope of my invention. The limits of the invention and the bounds of the patent protection are measured by and defined in the following claims. The restrictive description and drawing of the specific example above do not point out what an infringement of this patent would be, but are to enable the reader to make and use the invention.

As an aid to correlating the terms of the claims to the exemplary drawing, the following catalog of elements is provided:

| | |
|---|---|
| 10 RF generator | 30 alarm wire |
| 12 patient | 32 metal strip |
| 14 grounding pad | 34 RF ground contact |
| 16 alarm | 36 alarm ground contact |
| 18 probe | 38 wire |
| 20 outer band | 40 wax |
| 22 container | 42 alarm contact |
| 24 gel | 44 Nand gate |
| 26 ground wire | 46 battery |
| 28 alarm ground | 48 signal |

I claim as my invention:

1. The method of preventing burns at a grounding pad during use in an electrosurgical procedure comprising:
   a. monitoring the temperature at the grounding pad during the procedure, and
   b. activating an alarm when the monitored temperature of the grounding pad exceeds a predetermined limit.

2. The invention as defined in limitations a. through b. of claim 1 further comprising:
   c. activating said alarm when said temperature exceeds said limit for a preset time.

3. The invention as defined in limitations a. through b. of claim 1 wherein:
   c. the temperature is monitored by melting insulation from an insulated conductor in thermal contact with the grounding pad.

4. The invention as defined in limitations a. through c. of claim 3 wherein
   d. said conductor is immersed in a conducting gel.

5. The invention as defined in limitations a. through c. of claim 3 wherein
   d. said conductor is a wire which comes in electrical contact with a second conductor after the insulation melts.

6. An electrosurgical device to determine the occurrence of a burn producing condition having
   a. a signal generator,
   b. an active electrode connected to said generator,
   c. a system ground on said generator, and
   d. a grounding pad with
      (i) a conductive medium of a gel that is adapted to contact the patient,
      (ii) said medium connected to said ground, and
      (iii) an outer perimeter having an adhesive surface that is adapted to contact the patient;
   wherein the improvement comprises:
   e. a temperature sensor in said medium,
   f. an alarm connected to said temperature sensor for sounding an alarm when the temperature exceeds a predetermined temperature.

7. The invention as defined in limitations a. through f. of claim 6 wherein said temperature sensor includes:
   g. a conductor and
   h. an insulating material coating said conductor,
   i. said insulating material having a melting point at said predetermined temperature.

8. The invention as defined in limitations a. through i. of claim 7 further comprising:
   j. said conductor being a wire,
   k. said insulating coating being a wax having less than 0.5 mm thickness.

9. The invention as defined in limitations a. through k. of claim 8 further comprising:
   1. said wax being selected from a paraffin of the methane series having a melting point of less than 66° C.

* * * * *